(12) United States Patent
Apolet et al.

(10) Patent No.: US 9,387,127 B2
(45) Date of Patent: Jul. 12, 2016

(54) SKIN LESION PROTECTOR

(71) Applicants: Josek Berek Apolet, Milan (IT); Jonathan Byron, Beer-Sheva (IL); Ofer Spottheim, RaAnana (IL)

(72) Inventors: Josek Berek Apolet, Milan (IT); Jonathan Byron, Beer-Sheva (IL); Ofer Spottheim, RaAnana (IL)

(73) Assignees: Josek Berek Apolet, Milan (IT); Jonathan Byron, Beer-Sheva (IL); Ofer Spottheim, RaAnana (IL)

( * ) Notice: Subject to any disclaimer, the term of this patent is extended or adjusted under 35 U.S.C. 154(b) by 0 days.

(21) Appl. No.: 14/352,373

(22) PCT Filed: Oct. 22, 2012

(86) PCT No.: PCT/EP2012/070859
§ 371 (c)(1),
(2) Date: Apr. 17, 2014

(87) PCT Pub. No.: WO2013/057309
PCT Pub. Date: Apr. 25, 2013

(65) Prior Publication Data
US 2014/0309575 A1 Oct. 16, 2014

(30) Foreign Application Priority Data
Oct. 21, 2011 (EP) ..................................... 11186239

(51) Int. Cl.
*A61L 15/28* (2006.01)
*A61F 13/02* (2006.01)
*A61F 13/00* (2006.01)

(52) U.S. Cl.
CPC ......... *A61F 13/023* (2013.01); *A61F 13/00063* (2013.01); *A61F 13/0246* (2013.01);
(Continued)

(58) Field of Classification Search
USPC ................ 602/41–47, 54–56; 424/78.06, 473
See application file for complete search history.

(56) References Cited

U.S. PATENT DOCUMENTS 5,106,362 A * 4/1992 Gilman ........................... 602/47
5,447,492 A * 9/1995 Cartmell et al. ................ 602/58
(Continued)

FOREIGN PATENT DOCUMENTS

| WO | WO 2005/027859 | 3/2005 |
| WO | WO 2011/008360 | 1/2011 |
| WO | WO 2013/057309 | 4/2013 |

OTHER PUBLICATIONS

International Search Report and the Written Opinion Dated Jan. 30, 2013 From the International Searching Authority Re. Application No. PCT/EP2012/070859.
(Continued)

*Primary Examiner* — Ophelia A Hawthorne

(57) ABSTRACT

A device for the protection of skin lesions of various kinds, in particular lesions following biopsy interventions, comprising: a first sheet having a central opening; a spacing element on the first sheet, made of a non-rigid material soaked with substances having bacteriostatic, bactericidal, germicidal or fungicidal activity, and having a central opening of smaller size than the central opening in the first sheet, and the center of which is essentially coincident with the center of the opening in the first sheet, so that part of the spacing element comes into contact with the skin in an area surrounding the lesion; and a second sheet, made with a material having microporosity preferably lower than 0.5 μm, placed over the spacing element so as to close the top of the central opening in said spacing element and to form, when the device is in contact with the skin, a closed chamber.

23 Claims, 5 Drawing Sheets

(52) U.S. Cl.
CPC .......... *A61F2013/00165* (2013.01); *A61F 2013/00234* (2013.01); *A61F 2013/00263* (2013.01); *A61F 2013/00391* (2013.01); *A61F 2013/00608* (2013.01); *A61F 2013/00855* (2013.01); *A61F 2013/00936* (2013.01)

(56) References Cited

U.S. PATENT DOCUMENTS

| | | | | |
|---|---|---|---|---|
| 5,629,014 | A * | 5/1997 | Kwiatek et al. | 424/449 |
| 5,685,834 | A * | 11/1997 | Barth | 602/75 |
| 5,713,885 | A * | 2/1998 | Jorgenson et al. | 604/385.201 |
| 6,093,160 | A | 7/2000 | Augustine et al. | |
| 6,203,563 | B1 * | 3/2001 | Fernandez | 606/215 |
| 6,787,682 | B2 * | 9/2004 | Gilman | 602/58 |
| 8,247,635 | B2 * | 8/2012 | Sigurjonsson et al. | 602/54 |
| 2004/0243041 | A1 * | 12/2004 | Qin et al. | 602/41 |
| 2005/0186262 | A1 * | 8/2005 | Osborne et al. | 424/449 |
| 2008/0215026 | A1 * | 9/2008 | Schornick et al. | 604/369 |
| 2010/0312159 | A1 * | 12/2010 | Aali et al. | 602/44 |

OTHER PUBLICATIONS

European Search Report and the European Search Opinion Dated Feb. 16, 2012 From the European Patent Office Re. Application No. 11186239.

International Preliminary Report on Patentability Dated May 1, 2014 From the International Bureau of WIPO Re. Application No. PCT/EP2012/070859.

* cited by examiner

SKIN LESION PROTECTOR

FIELD OF THE INVENTION

The present invention is about a device for the protection of skin lesions, in particular, but not only, complex lesions following skin biopsy.

STATE OF THE ART

The formation of skin lesions (scratches, ulcers, cuts, wounds, both accidental and due to surgical interventions, such as for the removal of moles, melanomas, basal-cell carcinomas, squamous cells tumors, . . . ) transforms the involved body areas into areas especially exposed to attack of potentially harmful external agents, such as chemicals, physical agents, viruses, biological agents (germs, bacteria, fungi, . . . ), or UV radiations, the latter having mutagenic effect on the body cells. In particular, protection against UV rays is of the utmost importance in case of biopsies for the removal of skin tumors; in fact, the skin is capable to protect the underlying tissues from the action of UV rays, but in parts in which this protection is lost due to wounds of any kind, the incident radiations may ionize DNA molecules, giving rise to genetic mutations. It has been observed that UV irradiation of wounds caused by biopsies is responsible of a great deal of tumor recurrence.

Any time a skin lesion is formed, defense and reparation mechanisms are activated, directed to healing of the same. These mechanisms comprise the conveyance of increased amounts of blood with all its components in the lesion area, having, among others, the object of favoring phenomena that take part in the activation of platelets, in the formation of clot, and in the inflammation process; through these phenomena, in the area of the lesion are transported enhanced amounts of oxygen (useful for reparation mechanisms), of macrophages (for defense against pathogen agents) and of platelets (in order to favor haemostasis in the area of the lesion). The result is the rather fast formation of scabs, which are then replaced by the slower growth of granulation tissue.

The formation of clot and of the protecting granulation tissue require anyway different time spans, that may be of about a hour in case of less important lesions. For more serious or wide lesions, times up to hours or days are instead required, depending also on factors such as age, metabolism, blood circulation in the lesion area and in the surrounding area, and general conditions of the patient, and the zone of the lesion. Moreover, particularly in case of deep or wide lesions, the tissue reparation process may not be completely effective, and the lesion area could be exposed anyway to various noxious agents and infections; in such a case, in particular if necrosis even of minor entity occurs, it becomes necessary to remove the necrotic tissue (an operation known in the field as "debridement") in order to intervene immediately afterwards with curative treatments.

It is thus often necessary to protect the area of the lesion from various external noxious agents during the healing process.

Protection is generally realized with bandages or patches, capable to adjust to the body shape and movements, avoiding both that the lesion comes in contact with the external agents mentioned above, and its mechanical compression.

These protection means generally comprise bandages or adhesive strips having the function of retaining a pad in the desired position over the lesion, the pad being in form of a lint or compress of sterile material; these protection means may be possibly medicated (advanced medications), and may by made of different materials, such as hydrocolloids, hydrogels, polyurethane foam, collagen, paste or powders, alginates, hydrofibers, or carbon-based. Bandages and patches of this kind have however the drawback that the pad, normally having a fibrous structure, adhere or are even intermingled, at least partially, in the wound; as a consequence, when bandages or patches are removed for change with clean ones or for periodical medications (generally any 1-2 days), the scab is removed partially or completely as well, with re-opening of the wound and consequent stop and delay of the healing process, with the possible result of non-aesthetic scar formation in the area of the wound. Bandages and patches have been proposed having the part intended to come into contact with the lesion having chemical and morphological (smooth surface) characteristics such as to minimize or even avoid adhesion to the scab, but it has been observed that materials of this kind negatively affect scab formation.

Besides, it has been noted that the best conditions for recovery of a skin lesion are those as similar as possible to exposure to free air, that however, as stated above, has the problem of exposing inner parts of the body to the various noxious external agents.

An ideal protection for a skin lesion, during reparation process, should thus allow gases exchange with the outside, in particular the inlet of oxygen towards the lesion and the outlet of carbon dioxide and water vapor; prevent (or reduce as much as possible) the passage of solid particles, liquids, bacteria or viruses towards the lesion area; do not stick to the wound surface and obviously not to be itself a source of contamination; have bacteriostatic capabilities, and preferably show a bactericidal, fungicidal, or similar activity; and finally prevent, or reduce as much as possible, UV irradiation of the wound.

Some devices for the protection of skin lesions are known which fulfill a few of the above described needs.

U.S. Pat. No. 4,667,666 and International patent application WO 89/04158 disclose devices protection for protection of skin areas presenting lesions. These devices are made of a perimetrical basis intended to come into contact with the skin surrounding the lesion; a stiff and relieved central part is connected to the basis, covering the lesion but is kept at a distance from the same; said central part has punctures, having the function of allowing gas transport towards the chamber defined between said central part of the device and the skin. These devices however cannot avoid, or effectively reduce entrance of small size solid particles, of liquids, and the less of bacteria or viruses.

Patent application GB 2,303,304 discloses a device similar to the ones of the two previous documents, in which the relieved central part is formed of a fabric (e.g., linen or lint) made rigid e.g. by means of starch. This system, compared to the two ones described above is more impervious to solid particles, but does not overcome the other cited drawbacks.

U.S. Pat. No. 5,562,107 discloses a rather complex system that enables continuous inspection of a lesion and medication of the same, avoiding the need of removing the protection device. This device is made of a perimetrical frame intended to come into contact with the skin, in an area surrounding the lesion; onto the frame a transparent window is hinged, completely covering the central zone of the device and thus the lesion, when this is fixed to the skin. The window is fixedly connected to the frame along a side, and reversibly (by means of a weak adhesive) along the other sides, so that the window may be raised to accede to the lesion for medications, leaving the overall device always in its position. This device has however the drawback that the central window does not block the UV radiation, living rise to the aforementioned dangers of mutagenicity and, above all, of recurrence of tumors following biopsies; besides, the window is not porous enough to allow a continuous and effective exchange of oxygen, water vapor and carbon dioxide between the closed chamber defined by the window and the outside.

Patent application EP 2,161,011 describes a wound cover, that is not however designed for adhering to the skin, but rather to be part of a garment to be worn by a patient in the area of the wound. In fact, the device of this application has not a layer of adhesive material for attachment to the body (as explicitly stated in par. [0027]); the device of this application has openings that may be rather big (see, e.g., holes 5 in FIG. 11, in connection with par. [0053] of the description), thus allowing inlet of liquids, that is not desirable in the process of wound healing; and, the device of this application does not offer protection against UV irradiation (the metal filaments mentioned in par. [0069] are simply shape-stabilizing reinforcements, and by no means form a screen against light radiation, of any wavelength).

U.S. Pat. No. 6,093,160 describes a rather complex wound protection device. Similarly to the one of EP 2,161,011, this does not offer protection against UV irradiation, having a central "window" (element 20) as closing element of the upper part of the device; besides, this window is said "col. 6, lines 5-6" to be made of a thin film of polyethylene, that has not the desired property of easily allowing exchange of gases with the outside, thus leading to stagnation of gases in the chamber defined over the skin by the device, that, as discussed in the introduction, is not desirable for the process of wound healing.

Finally, U.S. Pat. No. 7,784,467 discloses a device for the protection of skin lesions against potentially harmful sunlight; this document, however, does not deal with the problem of maintaining a correct atmosphere above the lesion, by selective inlet of gases and vapors from the outside of the device towards the lesion area and vice versa; besides, in an embodiment thereof, the device of this document comprise a spongy part intended to come into direct contact with the lesion, thus causing the problems of adhesion to the wound described above.

Another main drawback common to most devices disclosed in the cited documents is that these comprise a relieved part, intended to keep the protection spaced apart from the wound, which is made of a rigid material; most systems described above are realized in such a way that this spacer is kept in the desired position from above and pushed against the skin. This way, a compression results of tissues in an area surrounding the wound, leading locally to a reduced blood circulation and possible necrosis of tissues in the same area.

SUMMARY OF THE INVENTION

It is thus an object of the present invention of providing a device for the protection of skin lesions, particularly those consequent to biopsy interventions, that overcomes the drawbacks of the known art.

In particular, it is an object of the invention to provide a device for the protection of skin lesions that, when applied to the skin, does not come into contact with the lesion, allows unrestrained exchange of gases between the lesion area and the outside thus maintaining about the lesion an atmosphere similar to the external gaseous ambient, avoids (or reduces to a minimum) the passage of solids, liquids, bacteria, viruses and UV radiation towards the lesion area, and avoids compression of the tissues surrounding the lesion.

This object is obtained according to the present invention with a device for the protection of skin lesions comprising:

- a first sheet of a flexible and gas-permeable material having an opening in its central part, and on a skinside face of which is present a discontinuous deposit of an adhesive material;
- a spacing element of thickness between 0.5 and 2 cm and having lateral size equal to or lower than that of said first sheet, being soaked, or being covered with a material soaked, with a substance having biocidal activity, said spacing element having an opening in its central part of smaller size than the opening in said first sheet;
- a second sheet, permeable to gases but impermeable to liquid water and made of, or comprising, a metallized material opaque to UV rays, placed over said spacing element and fixed either to the spacing element, or to the first sheet along a perimeter surrounding the contact area between said spacing element and said first sheet;
- said spacing element placed onto the outside face of the first sheet opposite to the one where the adhesive material is present and in such a position that the perimeter of the opening in the spacing element is completely encircled in the perimeter of the opening of the first sheet, and with an arrangement such that its outer edge is protected from contact with the external atmosphere.

By the definition "biocidal activity", in the present description and in the claims it is meant bacteriostatic, bactericidal, germicidal or fungicidal activity, or a combination of two or more of these; the substances having biocidal activity, preferred in the present invention, are metals or metal salts.

The spacing element may have lateral size equal or lower than that of the first sheet; in the first case, the second sheet is adhered to the surface of the spacing element opposite to the one that is in contact with the first sheet; in the second case, the perimetrical area of the second sheet is adhered to the first sheet along a line or area that is external to the outer edge of the spacing element, so that the latter is completely contained and held in position by the joining between the first and second sheets.

The second sheet, which must have the properties of being permeable to the passage of gases and water vapor but impermeable to liquid water, and opaque to UV rays, may be made of a single layer; alternatively, the second sheet may be obtained by the joining of two or more layers, such that their assembly ends up endowed of the needed characteristics cited before.

BRIEF DESCRIPTION OF THE FIGURES

The invention will be illustrated below with reference to the following figures.

DETAILED DESCRIPTION OF THE INVENTION

In the figures described below, sized are not in scale, and in particular some thicknesses are greatly enlarged, in order to make evident some details of the device of the invention. In the figures representing different embodiments of the device of the invention, same numerals indicate same or equivalent elements.

Figure 1:
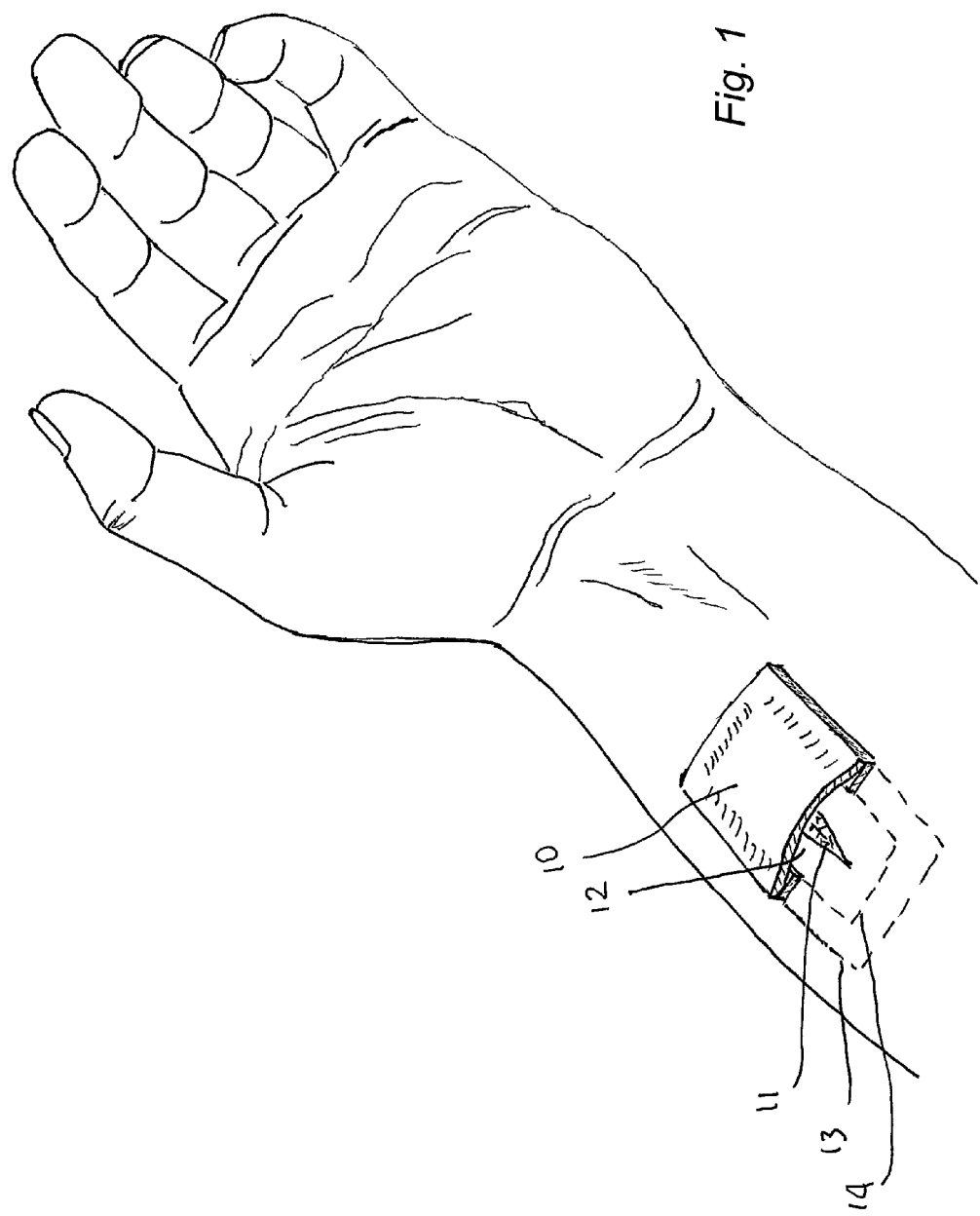
FIG. 1 represents, in a cut-away view, a device of the invention positioned to protect a skin lesion.

FIG. 1 shows in a cut-away view a device of the invention, 10, positioned above a skin lesion 11 (for instance, of the inner part of a forearm); the portion of device 10 above the lesion 11 is raised so that, in correspondence of the lesion, between the device and the skin a chamber, 12, is formed; the dotted lines 13 and 14 represent the track of the complete outer and inner contour, respectively, of the portion of the device being in contact with the skin.

Figure 2:
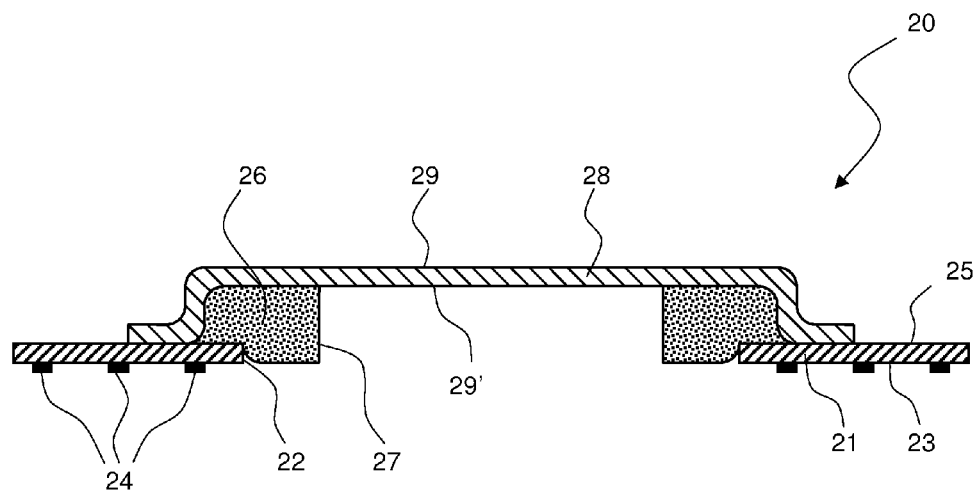
FIGS. 2 to 7 represent, schematically and in section, various different possible embodiments of the skin lesion protecting device of the invention.

A first and simpler embodiment of the device of the invention is represented in FIG. 2. This device, 20, comprises a first sheet 21 of a flexible and gas-permeable material having an opening, 22, in its central part. Opening 22 may have any shape; the most common opening shapes are circular, elliptical or oval, or essentially square or rectangular, but the opening may have other and more complex shapes, in order to protect in the best suitable way lesions of irregular shape.

The material sheet 21 is made of must be permeable to gases, in order to allow in particular the passage of oxygen from the outside towards the skin underneath, and the passage in the opposite direction of water vapor released by the skin; inflow of oxygen towards the skin is necessary to avoid the growing of colonies of anaerobic bacteria, which are extremely dangerous, further to improving the oxygenation of all tissues and components favouring the perfect healing of the wound, whilst the ease of water vapor removal avoids maceration of skin. Preferred materials for the production of sheet 21 are the non-woven-fabrics, made in particular of natural or semi-natural fibers such as cotton or viscose, but the adoption of synthetic fibers is possible as well. Typically, sheet 21 has thickness values comprised between 50 and 1000 micrometers (μm), and preferably between 100 and 500 μm.

Onto a skinside face, 23, of sheet 21, intended to come into contact with the skin, is present a discontinuous deposit of an adhesive material, 24. The adhesive is any of the ones known in the field, hypoallergenic and suitable for prolonged contact with the skin, for instance solventless acrylic-based adhesives or with water-based solvent; alternatively, other useful adhesives are the hydrocolloids known for this use, or even special adhesives containing already biocidal compounds, e.g., chlorhexidine or povidone-iodine. Adhesive 24 is present on face 23 of sheet 21 in a discontinuous fashion, in order to guarantee maximum breathability of some parts of the sheet surface, kept free from the adhesive. The adhesive may be deposited onto the sheet according to different patterns, for instance along parallel lines (in this case, for instance, adhesive deposits about 1 mm wide, spaced apart by about 1 mm, can be adopted), along zig-zag lines, or according to more complex patterns, for instance adjacent squares. The purpose of the adoption of more complex patterns is to reduce as much as possible the entrance of bacteria (or biological noxious agents in general) towards the area of the lesion, in direction parallel to the skin; it has been anyway observed that even the simple pattern of parallel lines is capable to lower the entrance rate of bacteria down to such levels that the bacteria are efficiently tackled by the leucocytes present in the same area.

Figure 8:
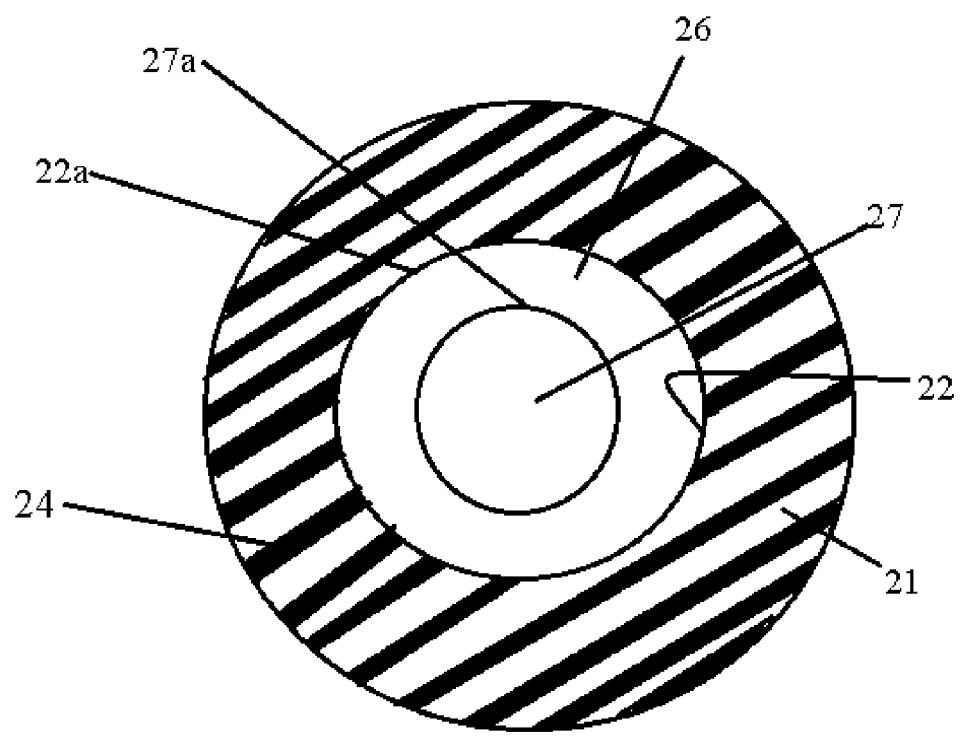
FIG. 8 is a bottom view of the device represented in FIG. 2.

With additional reference to FIG. 8, there is shown a bottom view of device 20. While device 20 is shown having a circular shape, it will be appreciated that this is a non-limiting example, and that other embodiments f the invention may have a rectangular shape or a square shape, as discussed further herein.

Device 20 is shown having a circular opening 22. A spacer element, 26, rests onto an outside face 25 of sheet 21 opposite to the one where the adhesive 24 is present. This element (also simply referred to as "spacer" in the following) has in its turn a central opening, 27 having a perimeter 27a which is completely encompassed by a perimeter 22a of the opening 22 in sheet 21, so that a part of element 26 extends beyond opening 22 in sheet 21 and comes into contact with the skin in an area surrounding the lesion; preferably, the center of opening 27 is essentially coincident with the center of opening 22. The shape of opening 27 is essentially correspondent to the shape of opening 22, and thus it will commonly be circular, elliptical or oval, or essentially square or rectangular, but other more complex shapes are possible. The lateral size of element 26 is lower than that of sheet 21, so that the outer border of element 26 is completely comprised in the surface of the first sheet. Element 26 contains or has on its surface a material or a substance (e.g., a metal) endowed with biocidal activity, that is bonded to element 26 in such a way to be slowly released to the skin; for instance, it can be a metal salt distributed in the spacer matrix, preferably soluble in water, so as to be dissolved by skin perspiration; or, it can be a thin metal deposit on the surface of element 26, obtained for instance by evaporation or CVD (Chemical Vapor Deposition). Metals useful for the objects of the present invention are, e.g., gold, copper and, especially, silver. Metal ions released by element 26 on the skin form a further barrier to lateral entrance (between the skin and skinside face 23 of sheet 21) of bacteria towards the lesion; besides, these ions may diffuse towards the area of the lesion, contributing to the anti-septic action in the same area.

Element 26 is preferably made of a non completely rigid material, such as, for instance, non-woven fabric felts or "fluff", namely, fiber flocks, compressed in order to have enough mechanical strength to keep the second sheet spaced apart at the desired distance from the lesion. The thickness of spacer 26 may vary, particularly depending on the lateral size of device 20; in fact, as the second sheet of the device is at least partially flexible as well, the wider the opening 27, the easier distortions or curvatures of the second sheet could bring this in contact with the lesion; as a consequence, the thickness of spacer 26 increases with the increasing of lateral size of device 20. Thickness values of spacer 26 useful for the aims of the invention are comprised between 0.5 and 2 cm.

To the first sheet 21 is fixed a second sheet, 28, along a closed line or area that completely encompasses the outer border of spacer 26, so that the latter is kept in the designed position between said first and second sheet. The fixing of sheets 21 and 28 to one another is obtained by means of adhesives; in case the materials of the two sheets 21 and 28 do not adhere effectively, it is possible to add an adhesion ring made of non-woven-fabric to guarantee a secure fixing. In case of further adhesion problems between said sheets, it is possible to adopt the technique of micronails-piercing aided coupling.

With this arrangement, the double result is obtained that the second sheet stays kept apart from the lesion, and holds element 26 in the desired position. In order to guarantee the correct positioning of spacing element 26 in device 20, particularly with respect to opening 22 in the first sheet, it is also possible to fix, by means of an adhesive, the spacing element to the first and/or second sheet.

The second sheet is however not taut over spacer 26, to avoid exerting pressure on the latter, which would result in the compression of the skin in the area corresponding to the position of element 26, with consequent reduced blood flow and necrosis of this area. The only possible pressure on the skin, localized in an area corresponding to the position of spacer 26, may come from the weight of clothes or of the body itself (when the patient lays on the lesion area); if the patient is instructed to avoid, or reduce as much as possible, these two source of pressure, the device of the invention does not cause any compression of the area surrounding the lesion, and thus no necrosis or healing delay of the same.

The second sheet 28, in its central part, is raised and spaced apart from the level of the first sheet by means of spacer 26; the result is that, when device 20 is positioned onto the skin, said second sheet does not come into contact with the lesion, and forms with the skin a chamber (element 12 in FIG. 1) protecting the lesion. Sheet 28 may have the same width of sheet 21; this embodiment simplifies the production process of the device, as it allows assemblies of big size to be manufactured, made of a plurality of devices of kind 20 next to each other in the assembly, an to separate the final protecting devices by simply cutting the assembly along preset lines, for instance by using a press punch or a linear rotating hollow punch.

Alternatively, sheet 28 may have a lower size than sheet 21, and be fixed to the latter along a closed line or zone comprised between the outer border of spacer 26 and the outer perimeter of sheet 21; this embodiment allows a saving of the amount of material of the second sheet. FIG. 2 (and the subsequent FIG. 3) represent devices according to this second embodiment, but it is understood that the invention covers devices according to the first embodiment as well.

In both embodiments (sheets 21 and 28 of same dimensions, or sheet 28 of lower size than sheet 21), sheet 28 has no contact points to the skin.

Sheet 28 must have micro-porosity, of size preferably lower than 0.5 μm. Water surface tension is such that droplets of size below the indicated values cannot remain cohesive and are transformed into water vapor; this prevents thus mass transport of water and water solutions (the liquids most commonly present in the ambient) towards the lesion, which could lead to maceration of the same; besides, this size allows to prevent entrance in chamber 12 of essentially all solid particles and noxious biological agents. On the other hand, apertures of this size allow free flow of gases, in particular oxygen, between said chamber and the outer ambient, depending on the gradient of concentration (or partial pressure) of gases across the device; this way, it is guaranteed that the gaseous ambient inside the chamber is constantly in equilibrium with the outer atmosphere (and thus essentially identical to the latter), that, as stated before, is the ideal one for the recovery of skin lesions. Typically, sheet 28 has thickness values comprised between 50 and 1000 μm.

These characteristics can be obtained with sheets of expanded polytetrafluoroethylene, marketed for instance by the US company W. L. Gore & Associates, that are known for having this very feature of allowing gas and water vapor passage but not of water in liquid form. Alternatively, sheet 28 may be produced with perforated polyurethane or polyethylene foils.

The material the second sheet is made of is then metallized, for instance by aluminum evaporation, in order to make it reflecting and opaque to UV rays. Sheet 28 may be aluminized on its outside face 29, on its skiside face 29' (facing chamber 12), or both; preferably, sheet 28 is aluminized at least on outside face 29.

Figure 3:
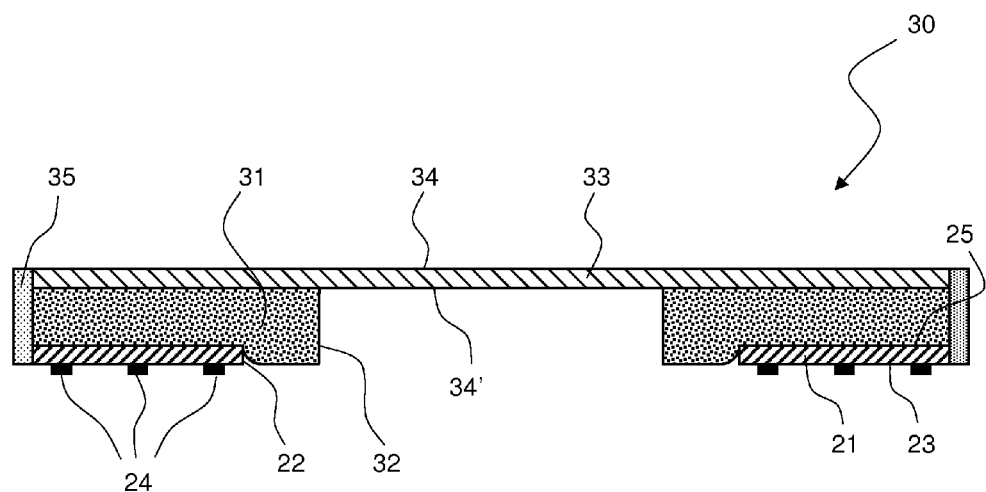

In a second embodiment, the spacing element has lateral size equal to that of the first sheet. This embodiment is schematically shown in FIG. 3. In this case the device, 30, is made of a first sheet 21 with a central opening 22; on a skinside face 23 of sheet 21, intended to come in contact with the skin, is present a discontinuous deposit of adhesive material, 24; in contact with an outside face, 25, of sheet 21, is present the spacing element, 31, that as said above has the same lateral size of sheet 21 and that has an opening, 32, of shape essentially corresponding to the one of opening 22, and the perimeter of which is completely encircled by the perimeter of the latter, so that a part of element 31 extends beyond opening 22 in sheet 21 and comes into contact with the skin in an area surrounding the lesion; preferably, the center of opening 32 is essentially coincident with the center of opening 22.

On the surface of spacing element 31 opposite to the one in contact with first sheet 21, a second sheet, 33, is fixed; sheet 33 may have the same lateral size of sheet 21 and of spacing element 31; or, it may have lower size but bigger than that of opening 32, and be fixed to spacing element 31 in such a way to completely close said opening 32 in its upper part; FIG. 3 illustrates the case in which sheet 33 has the same lateral size as the first sheet and the spacing element. Sheet 33 may be metallized on its outside face 34, on its skinside face 34' (in operation, towards chamber 12), or both.

Materials, thickness values and production methods of the elements making up device 30 (first sheet, adhesive deposited in discontinuous fashion on a skinside face of this, spacing element and second sheet) are equivalent to those of the analogous elements in device 20. The only difference between device 20 and device 30 is that in the latter, as said, spacing element 31 has the same lateral size of first sheet 21; this entails that spacer 31 is not contained in the assembly between the first and second sheets, so that all layers of the device must be fixed to the next ones with adhesives, possibly having recourse to the micronails-piercing aided coupling technique cited above, in cases in which adhesion of spacing element 31 to the first and/or second sheet is not satisfactory.

In device 30 the outer edges of spacing element 31 are essentially coincident with those of the device; as spacer 31 is highly porous, it could represent an inlet of liquids or even bacteria, fungi and viruses towards the lesion area. As a consequence, the exposed edge of spacing element 31 must be protected and made impervious to liquids (which assures the impossibility of passage of various bacteria and viruses as well); this condition can be realized e.g. by forming on said exposed edge (for instance by brushing) a layer 35 of an impermeable material, such as, e.g., an adhesive. The presence of layer 35 is necessary only on the exposed edge of element 31, but for production ease, this layer may be formed over the whole edge of device 30 (this is the condition shown in the figure).

In the device of kind 30, the possibility that the second sheet exerts a pressure onto the spacing element, with possible necrosis of the area surrounding the lesion, is ruled out by the very structure of the device.

Figure 4:
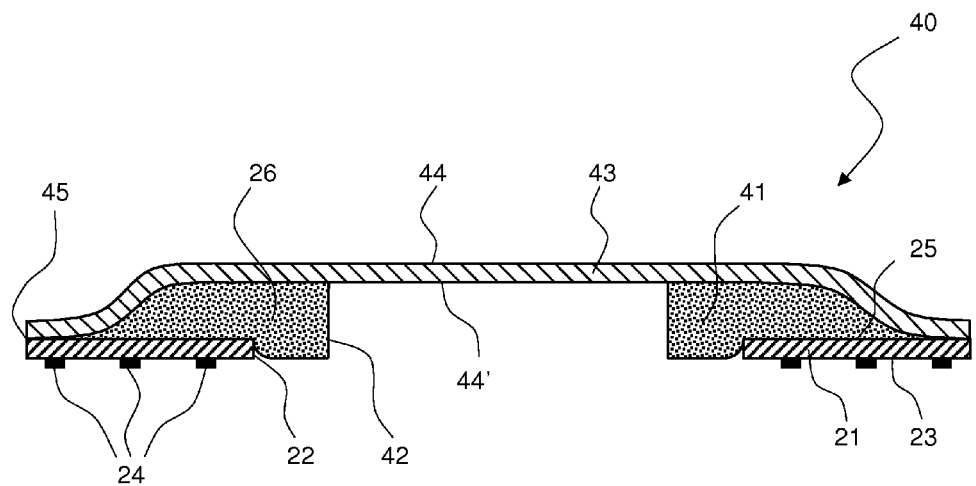

The protection of the outer edge of spacing element 31 can be achieved alternatively according to a third embodiment of the invention, schematically shown in FIG. 4.

The device according to this embodiment, 40, is made up of a first sheet 21 with a central opening 22; on a skinside face 23 of sheet 21, intended to come in contact with the skin, is present a discontinuous deposit of adhesive material, 24; in contact with an outside face, 25, of sheet 21, is present the spacing element, 41, that as in device 30 has the same lateral size of sheet 21 and that has an opening, 42, of shape essentially corresponding to the one of opening 22, and the perimeter of which is completely encircled by the perimeter of the latter, so that a part of element 41 extends beyond opening 22 in sheet 21 and comes into contact with the skin in an area surrounding the lesion; preferably, the center of opening 42 is essentially coincident with the center of opening 22.

On the surface of spacing element 41 opposite to the one in contact with first sheet 21, a second sheet, 43, is fixed, which may be metallized on its outside face 44 orientated outwards, on its skinside face 44' orientated towards the inside of the device (that is, in operation, towards chamber 12), or both. Along the perimeter 45 of device 40, skinside face 44' of sheet 43 is fixed to outside face 25 of sheet 21.

Device 40 may be produced from an assembly made by stacking first sheet 21, spacing element 41 and second sheet 43, said assembly having lateral size greater than that of the final device 40, and separating device 40 from the assembly by hot milling with a suitably shaped punch. Hot milling cuts the assembly along a pre-set close line, corresponding to the perimeter 45 of device 40, locally compresses spacer 41 reducing its thickness to a much reduced value compared to the starting one, and realizes the localized melting of sheet 43, of spacer 41 and of sheet 21; by means of this melting along perimeter 45 of the device, spacing element 41 ends up to be contained between sheets 31 and 43 and not exposed, at its borders, to the passage of liquids, bacteria or viruses. The punch by which hot milling along perimeter 45 is performed preferably has such a shape that it comes into contact with the assembly only in the area corresponding to the perimeter of device 40, and not with the center of the latter as well; the reason is that, if the punch came in contact with the whole outer face, 44, of sheet 43, this could alter its chemical and mechanical properties, and in particular this could cause surface melting that would lead to clogging, totally or in part, the micro-porosity of said sheet.

Also in case of device 40, materials, thickness values and production methods of the elements it is made up of are the same of the equivalent elements of devices 20 and 30.

The second and third embodiments of the invention are more suitable than the first one for the production of devices of relatively small size; devices of kind 30 and 40 may be conveniently produced, for instance, in rectangular shape with size of about 19×72 mm, 25×72 mm, 60×75 mm, 60×100 mm, or in square or round shape with side or diameter of about 20, 25, 40, 60, 80 and 100 mm; these sizes are anyway non-limiting examples, and the device of the invention may clearly be produced also with sizes different from those cited above, depending on need. Vice versa, devices of the first embodiment (devices of kind 20) are more suited for the production in greater size. The reason is that the structure of a device of kind 30 or 40 allows to produce a big size assembly of the three elements, first sheet, spacer and second sheet, joined all over their surface, and to obtain the single devices of kind 30 by cutting the assembly along lines equally spaced from openings 22 and 32, and the single devices of kind 40 by hot milling along lines equally spaced from openings 22 and 42. The assembly may be produced in discrete format (big size sheets), or in tapes. The ease of production, and thus the cost savings, of these embodiments compared to devices of kind 20 balances out the use of greater amounts of material for the production of spacing element 31 or 41. For the same reason, even if as stated above the second sheet, 33 or 43, could have lower size than that of first sheet and of spacing element, from the production standpoint turns out to be preferable that the second sheet too has the same lateral size of the other two cited elements.

In devices 20, 30 and 40 described so far, the second sheet (28, 33 or 43) is made of a material in single layer, but according to the invention the second sheet may be made up of two or more paired layers, of same or different materials, each one realizing at least one of the functions of the second sheet. Devices embodying this feature are described below. In this description and in the corresponding figures, reference will be made to the case of a second sheet made up by the pairing of two layers, but it is evident that said second sheet could be made of a higher number of layers.

Figure 5:
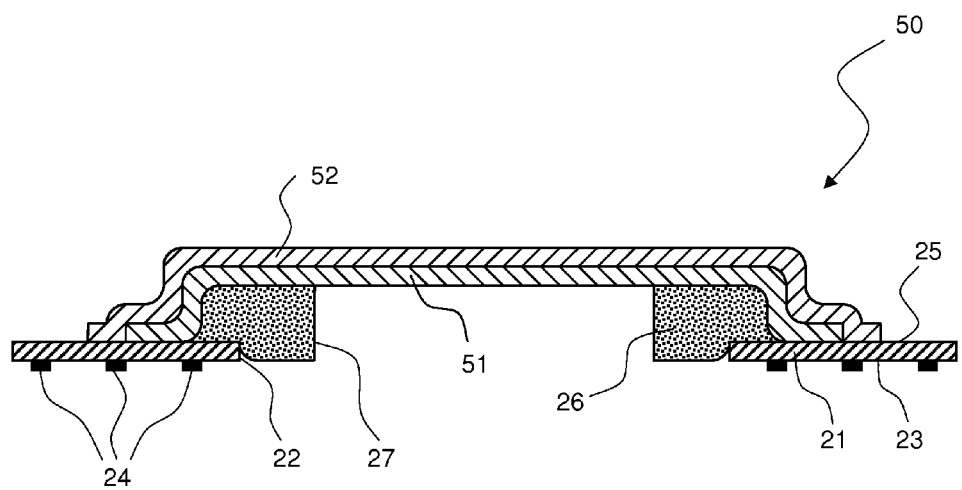

In a fourth possible embodiment, shown schematically in section in FIG. 5, the device of the invention, 50, has a construction similar to device 20 of the first embodiment, but in this case the function of the second sheet is carried out by two or more layers coupled to each other. The figure illustrates the case in which the second sheet is made up by two coupled layers, 51 and 52, which can be simply in contact with one another, and fixed to each other and with sheet 21 only along their border or in a perimetrical area thereof; in alternative, layers 51 and 52, after their production, may be caused to adhere over their entire surface, for instance by hot compression.

In this embodiment, one of the two layers (e.g., layer 51) may be a fabric or non-woven-fabric layer, made of natural or synthetic fibers, which is metallized to block UV rays, while the other one (in this case layer 52) is not metallized, and has the feature of being micro-perforated with holes of size below 0.5 μm. An exact stacking order of the two layers is not mandatory, and layer 52, shown in FIG. 5 as the outer one, could face the lesion instead. The only mandatory condition to be met is that, if the layer with micro-porosity of size (preferably) lower than 0.5 μm is the outer one, inner layer 51 (which could have porosity of bigger size, thus being permeable to liquids, bacteria and viruses) must be protected from the contact with the external atmosphere, for the reasons mentioned already with reference to device 30; this can be accomplished by producing layer 52 with lateral size greater than layer 51, and fixing the perimeter of the former directly to the first sheet 21 (case illustrated in the figure), or, alternatively, by producing layers 51 and 52 of same size and protecting the outer edge of layer 51 with a layer of an impermeable material, like layer 35 described for device 30. If, on the other hand, the layer with porosity of size (preferably) lower than 0.5 μm is the inner one, this measure is not necessary (because this layer is in direct contact with first sheet 21), and the two layers 51 and 52 may have the same size nor it is necessary to adopt a protection of the edge of kind 35. In case in which (as illustrated in the drawing) the metallized layer is the inner one, metallization is preferably present on its outside face contacting outer layer 52 (or at least on this face). To the contrary, in case the metallized layer is the outer one, 52, metallization can be present irrespectively on either of its faces, or both.

In the case of the device 50, the sum of the thickness values of layers 51 and 52 is typically variable between about 50 and 2000 μm, preferably between 50 and 1000 μm.

Figure 6:
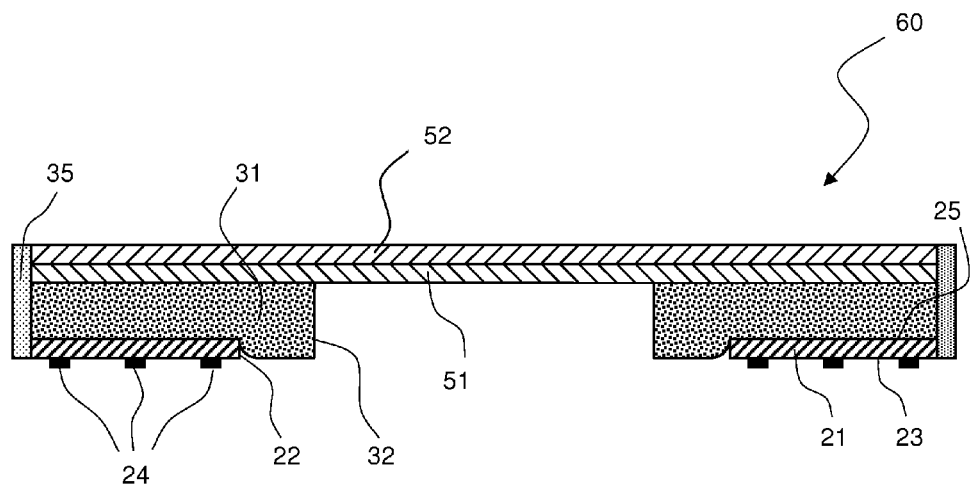

A fifth embodiment of the device of the invention is shown schematically in section in FIG. 6; in this figure, elements bearing the same numerals of those of the previous figures have the same meaning. The device or this embodiment, 60, has structure similar to device 30 (elements in FIG. 6 bearing the same numbers as those in FIG. 3 have the same meaning, construction and features of the latter), apart from the second sheet, that is made up by two or more layers 51 and 52 as in device 50.

Layers 51 and 52 may be fixed to each other either only along their edges or perimetrical area, or on their whole surface. In device 60, materials, thickness values, production methods and reciprocal arrangement of layers 51 and 52 are as described for device 50. In this case too, as in device 30, the exposed edge of the spacing element 31 must be protected with a layer, 35, of a material impermeable to liquids, bacteria and viruses (materials of layer 35 in device 60 are the same previously mentioned in the description of device 30).

Figure 7:
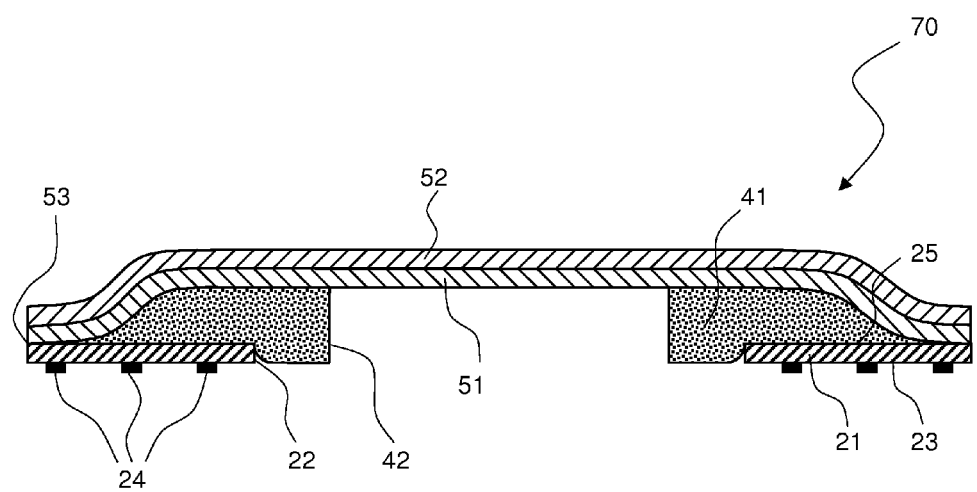

Finally, in a sixth possible embodiment, the device of the invention has the structure schematically shown in FIG. 7. This device, 70, has the same geometry, and is produced by the same method (hot milling) of device 40; elements in FIG. 7 bearing the same numbers as those in FIG. 7 have the same meaning, construction and features of the latter. In device 70, hot milling of the starting assembly creates the perimeter 53 of the device. The only difference between device 70 and device 40 is that in the former the second sheet is made up by the coupling of two or more layers; the example in the figure shows a second sheet obtained by the coupling of two layers, 51 and 52. Materials, thickness values, production methods and reciprocal arrangement of layers 51 and 52 (or more layers, in case the second sheet is formed by more than two of these) are as described for device 50.

The invention claimed is:

1. A device for protection of skin lesions, comprising:
   a first sheet of a flexible and gas-permeable material having an opening in its central part, said first sheet having an outside face and a skinside face opposite said outside face, a discontinuous deposit of an adhesive material present on said skinside face, said first sheet opening having a first perimeter;
   a spacing element placed over the outside face of the first sheet, of thickness between 0.2 and 2 cm and having lateral size equal to or lower than that of said first sheet, being soaked, or being covered with a material soaked, with a substance having biocidal activity, said spacing element having an opening in its central part, said spacing element opening having a second perimeter of smaller size than said first perimeter, said spacing element placed onto and resting on the first sheet outside face in such a position that a center of said spacing element opening is coincident with a center of said first sheet opening, that said second perimeter is completely encircled in said first perimeter, and that a portion of the spacing element outside said second perimeter extends into the first sheet opening; and
   a second sheet, permeable to gases but impermeable to liquid water and made of, or comprising, a metalized material opaque to UV rays, placed over said spacing element and fixed either to the spacing element, or to the first sheet along a third perimeter surrounding a contact area between said spacing element and said first sheet, wherein said second sheet and said spacing element opening form a hollow chamber with one open face,
   with an arrangement such that an outer edge of the spacing element is protected from contact with an external atmosphere.

2. The device according to claim 1, in which said first sheet has a thickness comprised between 50 and 1000 μm.

3. The device according to claim 2, in which said spacing element has lateral size equal to that of the first sheet, and in which the second sheet skinside is fixed to the first sheet outside face along a perimeter of the first sheet and spacing element by means of localized hot melting of one or more of said first sheet, spacing element and second sheet.

4. The device according to claim 2, in which said spacing element has lateral size equal to that of the first sheet and is fixed with an adhesive to both the first and second sheet, and in which on the outer edge of said spacing element is present a layer of a material impermeable to a passage of liquids, bacteria and viruses.

5. The device according to claim 2, in which said spacing element has lateral size lower than that of the first sheet, the outer edge of the second sheet is fixed with an adhesive to the outside face of the first sheet opposite to the one on which said discontinuous deposit of adhesive material is present, and a joining between the first and second sheets is produced in a perimetrical area of the second sheet along a line or area external to the outer edge of the spacing element.

6. The device according to claim 1, in which said second sheet is made of a micro-porous material with pore size lower than 0.5 μm, metallized at least on one face thereof.

7. The device according to claim 6, in which said second sheet is made of expanded polytetrafluoroethylene or perforated polyurethane or polyethylene.

8. The device according to claim 6, in which said second sheet has a thickness comprised between 50 and 1000 μm.

9. The device as claimed in claim 1, in which the substance having biocidal activity is a metal or a metal salt.

10. The device according to claim 9, in which said spacing element has lateral size equal to that of the first sheet, and in which a skinside face of the second sheet is fixed to the first sheet outside face along a perimeter of the first sheet and spacing element by means of localized hot melting of one or more of said first sheet, spacing element and second sheet.

11. The device according to claim 1, in which said openings in the first sheet and in the spacing element have a corresponding geometrical shape.

12. The device according to claim 11, in which said spacing element has lateral size equal to that of the first sheet, and in which the skinside face of the second sheet is fixed to the first sheet outside face along a perimeter of the first sheet and spacing element by means of localized hot melting of one or more of said first sheet, spacing element and second sheet.

13. The device according to claim 1, in which said second sheet is made up by at least two layers in contact with each other, of which at least a layer is metallized and porous and at least a layer has pores with size lower than 0.5 μm.

14. The device according to claim 13, in which a sum of thickness values of layers making up the second sheet is comprised between 50 and 2000 μm.

15. The device according to claim 1, in which said first sheet is made of a non-woven-fabric of natural, semi-natural or synthetic fibers.

16. The device according to claim 1, in which said spacing element is made of a non completely rigid material, chosen among non-woven fabric felts, synthetic material felts, or fiber flocks, ("fluff").

17. The device according to claim 1, in which said spacing element is fixed with an adhesive to the first and/or second sheet.

18. The device according to claim 1, in which said spacing element has lateral size lower than that of the first sheet, an outer edge of the second sheet is fixed with an adhesive to the first sheet outside face, and a joining between the first and second sheets is produced in a perimetrical area of the second sheet along a line or area external to the outer edge of the spacing element.

19. The device according to claim 1, in which said spacing element has lateral size equal to that of the first sheet and is fixed with an adhesive to both the first and second sheet, and in which on the outer edge of said spacing element is present a layer of a material impermeable to a passage of liquids, bacteria and viruses.

20. The device according to claim 1, in which said spacing element has lateral size equal to that of the first sheet, and in which a skinside face of the second sheet is fixed to the outside face of the first sheet along a perimeter of the device by means of localized hot melting of said first sheet, spacing element and second sheet.

21. The device according to claim 1, in which said first sheet has a thickness comprised between 100 and 500 μm.

22. A method for protection of a lesion, comprising:
   (a) providing a device comprising:
      a first sheet of a flexible and gas-permeable material having an opening in its central part, said first sheet having an outside face and a skinside face opposite said outside face, a discontinuous deposit of an adhesive material present on said skinside face, said first sheet opening having first perimeter;
      a spacing element placed over the outside face of the first sheet, of thickness between 0.2 and 2 cm and having lateral size equal to or lower than that of said first sheet, being soaked, or being covered with material soaked, with a substance having biocidal activity, said spacing element having an opening in its central part, said spacing element opening having a second perimeter of smaller size than said first perimeter, said spacing element placed onto and resting on he first sheet outside face in such a position that a center of said spacing element opening is coincident with a center of said first sheet opening, that said second perimeter is completely encircled in said first perimeter, and that a portion of the spacing element outside said second perimeter extends into the first sheet opening; and a second sheet, permeable to gases but impermeable to liquid water and made of, or comprising, a metalized material opaque to UV rays, placed over said spacing element and fixed either to the element, or to the first sheet along a third perimeter surrounding a contact area between said spacing element and said first sheet, wherein said second sheet and said spacing element opening form a hollow chamber with one open face, with an arrangement such that an outer edge of the s racing element protected from an external atmosphere;

(b) positioning said opening in said spacing element over said lesion so said lesion is not contacted by said spacing element; and (c) mounting said device onto a wound using an adhesive property of said first sheet;

wherein said second sheet is fixed either to the spacing element or to the first sheet in a manner such that said device does not coin fess skin an area corresponding to a position of said spacing element.

23. The method as claimed in claim 22, wherein said second sheet is not taut over said spacer.

\* \* \* \* \*